(12) United States Patent
Wolfrum et al.

(10) Patent No.: US 8,318,860 B1
(45) Date of Patent: Nov. 27, 2012

(54) METHOD FOR FLUID-PHASE SYNTHESIS OF A POLYMER

(76) Inventors: Christian Wolfrum, Erlangen (DE); Wolfgang Prinz, Freistadt (AT)

( * ) Notice: Subject to any disclaimer, the term of this patent is extended or adjusted under 35 U.S.C. 154(b) by 0 days.

(21) Appl. No.: 12/679,274

(22) PCT Filed: Sep. 17, 2008

(86) PCT No.: PCT/EP2008/062337
§ 371 (c)(1),
(2), (4) Date: Sep. 17, 1998

(87) PCT Pub. No.: WO2009/037268
PCT Pub. Date: Mar. 26, 2009

(30) Foreign Application Priority Data

Sep. 19, 2007 (DE) .................. 10 2007 044 765

(51) Int. Cl.
*C08L 71/02* (2006.01)
(52) U.S. Cl. ....... 525/187; 525/403; 525/404; 536/25.3; 536/25.31; 536/25.34
(58) Field of Classification Search .......... 536/25.3, 536/25.31, 25.34; 525/403, 187, 404
See application file for complete search history.

(56) References Cited

U.S. PATENT DOCUMENTS 5,874,532 A * 2/1999 Pieken et al. ............... 530/338

OTHER PUBLICATIONS

Gravert, D.J.; Janda, K.D.; Chemical Reviews, 1997(97), p. 489-509.*
Blettner, "Polymergestutzte parallele Flussigkeitsphansensynthese", Thesis of Blettner, Carsten G., pp. 10-23, 1999.
Bonora et al., "Large scale, liquid phase synthesis of oligonucleotides by the phosphoramidite approach", Nucl. Acids Res., 21(5):1213-1217, 1993.
Cramer et al., "Oligonukleotid-synthese an einem Ioslichen Polymeren als Trager", Angewandte Chemie, 78, Jarg., (12):640-641, 1966.
Gravert, Dennis J. et al., "Synthesis on soluble polymers; new reactions and the construction of small molecules", Curr. Opin. In Chem. Biol., 1:107-113, 1997.
English Language Explanation of: Blettner, "Polymergestutzte parallele Flussigkeitsphansensynthese", Thesis of Blettner, Carsten G., pp. 10-23, 1999 (Effective date of Explanation: 1999).
English Translation of Cramer et al., "Oligonukleotid-synthese an einem Ioslichen Polymeren als Trager", Angewandte Chemie, 78, Jarg., (12):640-641, 1966 (Effective date of translation: 1966).

* cited by examiner

*Primary Examiner* — David W Wu
*Assistant Examiner* — Robert Jones, Jr.
(74) *Attorney, Agent, or Firm* — Fish & Richardson P.C.

(57) ABSTRACT

The invention relates to a method for the fluid-phase synthesis of a polymer formed from n monomers.

18 Claims, 5 Drawing Sheets p-chlorophenyl     o-chlorophenyl     β-cyanoethyl

METHOD FOR FLUID-PHASE SYNTHESIS OF A POLYMER

CROSS REFERENCE TO RELATED APPLICATIONS

This application is a national phase filing under 35 U.S.C. §371 of International application number PCT/EP2008/062337, filed Sep. 17, 2008, which claims priority from German application number 10 2007 044 765.7 filed Sep. 19, 2007. The entire content of the prior applications are incorporated herein by reference in their entirety.

BACKGROUND

The prior art discloses that deoxyribonucleic acid polymers are synthesized by attaching to a nucleotide which is immobilized via its 3' end to a solid support in each step a nucleotide to the present or newly produced 5' end, until an oligo- or polynucleotide of the desired length is formed. This oligo- or poly-nucleotide is then cleaved off the solid support. The solid support here is typically in a chromatographic column. The larger the column packing used here, the more difficult the process is to manage. More specifically, homogeneous packing of the column is difficult to achieve, and a powerful pump is required due to the loss of pressure along the flow path of large columns. Another problem is the edge effect which is always present in columns and which results in a chromatographic front migrating more slowly close to the wall of the column than in the center of the column, reducing the efficiency of the process.

Bonora, G. M. et al., Nucleic Acids Research, 1993, Volume 21, No. 5, pages 1213 to 1217 disclose, by way of an alternative method of synthesizing large amounts of DNA, a method for fluid-phase synthesis of oligo-nucleotides, which comprises using polyethylene glycol (PEG) as soluble support and phosphoramidite derivatives as synthons. This involves polyethylene glycol being bound to the 3' end of a nucleoside to be extended in the synthesis reaction. After a dimethoxytrityl protective group on the nucleoside has been removed, a condensation with a nucleoside phosphoramidite occurs at the 5' end of said nucleoside. The reaction product is precipitated and recrystallized. After capping and subsequent oxidation, the PEG-phosphate derivative obtained is precipitated, filtered and recrystallized. Said process steps of detritylation, condensation, precipitation, recrystallization, capping, oxidation, precipitation, filtration and recrystallization are then repeated until the polymer has the desired length. Finally, the polyethylene glycol is cleaved off and the oligonucleotide obtained is precipitated. The oligo-nucleotide is then dissolved and purified by ion exchange chromatography.

Both of the methods mentioned have the disadvantage of an exponential increase in the probability of producing an incorrect polynucleotide as a function of increasing chain length. This is due to the fact that in any one coupling or condensation step a small percentage of the nucleotide chains to be extended fails to react. Assuming a coupling efficiency of 98%, this results already in 18.3% incorrect oligomers for an oligomer formed from only 10 nucleotides. For a polymer formed from 100 nucleotides, already 86.7% of the polymers formed are incorrect. The incorrect polymers can thus greatly exceed the amount of correctly synthesized polymers. As a result, a large amount of effort is required to remove the incorrect polymers, for example by means of chromatography, in order to obtain the desired polymer in a pure form. Due to the purification required and the large amount of reagents inevitably used for producing incorrect polymers, producing a desired polymer is relatively expensive.

It is an object of the present invention to provide a method for fluid-phase synthesis of a polymer formed from monomers, by means of which method said polymer can be produced inexpensively in large quantities and with high purity.

SUMMARY OF THE INVENTION

This object is achieved by the features of claim 1. Useful embodiments of the invention arise from the features of claims 2 to 15.

The invention provides for a method for fluid-phase synthesis of a first polymer formed from n monomers, comprising the following steps:

a) providing a dissolved first compound, wherein said first compound is formed from a first monomer and a second polymer having a first specific solubility, wherein said first monomer and said second polymer are linked to one another by a first bond, wherein said first bond can be cleaved by a first cleavage reaction, wherein said first monomer has an active or an activatable first group, b) providing a dissolved second compound, wherein said second compound is formed from a second monomer and a third polymer having a second specific solubility, wherein said second monomer and said third polymer are linked to one another by a second bond, wherein said second bond can be cleaved by a second cleavage reaction, wherein said second monomer has an active or an activatable second group which, by way of a linking reaction, can react with the first group with formation of a third bond between the first and second monomers, wherein said first and second specific solubilities are different, c) contacting the first and second compounds in order for the linking reaction to occur, wherein, if the activatable first and/or the activatable second group are/is present, said first and/or said second group are/is activated by adding an activator, d) carrying out a precipitation reaction specific for the second or third polymer, and separating any first or second compound precipitated in the process and the reaction product formed in step c), e1) dissolving the separated first or second compound and the reaction product in a solvent, carrying out a precipitation reaction specific for the second or third polymer for which the precipitation reaction carried out in step d) was not specific, separating reaction products precipitated in the process, and dissolving the reaction product in said solvent or another solvent, or e2) contacting the separated first or second compound and the reaction product with a solvent in which essentially only the reaction product dissolves but in which the first or second compound precipitated in step d) essentially does not dissolve, f) carrying out the second cleavage reaction with the reaction product, wherein a further reaction product and the third polymer are formed, wherein the first active group is formed on said further reaction product, and g) (n−2)-fold repetition of steps b) to f), wherein the first compound is replaced by the further reaction product formed in step f), and the second compound is replaced in each case with a further compound, wherein said further compound is formed from a further monomer and the third polymer.

The further monomer and the second monomer may be different or identical. The first polymer may also be an oligomer. A precipitation reaction specific for the second polymer means a precipitation reaction in which the third polymer essentially remains in solution. A precipitation reaction specific for the third polymer means a precipitation reaction in which the second polymer essentially remains in solution. The reaction partners and the reaction product as well as the further reaction product are understood as meaning not only a single molecule but a multiplicity of molecules of the same type, even if the singular is used in referring to said molecules. Thus, for example, a multiplicity of identical first compounds and a multiplicity of identical second compounds are provided, resulting in a multiplicity of identical reaction products upon carrying out step c).

BRIEF DESCRIPTION OF THE DRAWINGS

Acetonitrile is used as solvent in the entire reaction described below.

Figure 1:
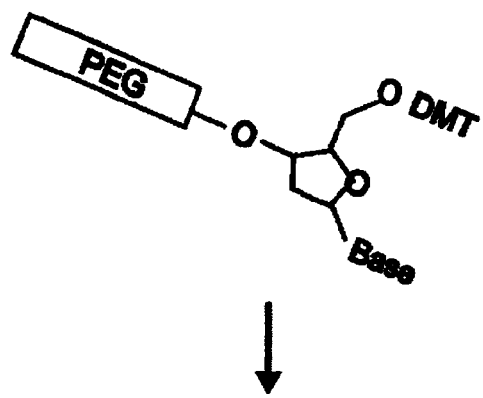
FIG. 1 depicts a nucleoside bound at its 3' carbon atom via an oxygen atom to a polyethylene glycol (PEG) group. At its 5' carbon atom, said nucleoside has a dimethoxytrityl (DMT) protective group bound via a further oxygen atom. The 5' oxygen atom having the DMT protective group represents an activatable group. The DMT protective group is cleaved off by means of a weak organic acid such as, for example, dichloroacetic acid, thereby forming a free OH group as active group. The corresponding reaction product is depicted as first compound in FIG. 2.
Figure 2:
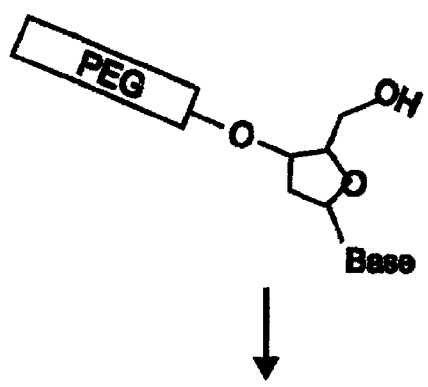
Figure 3:
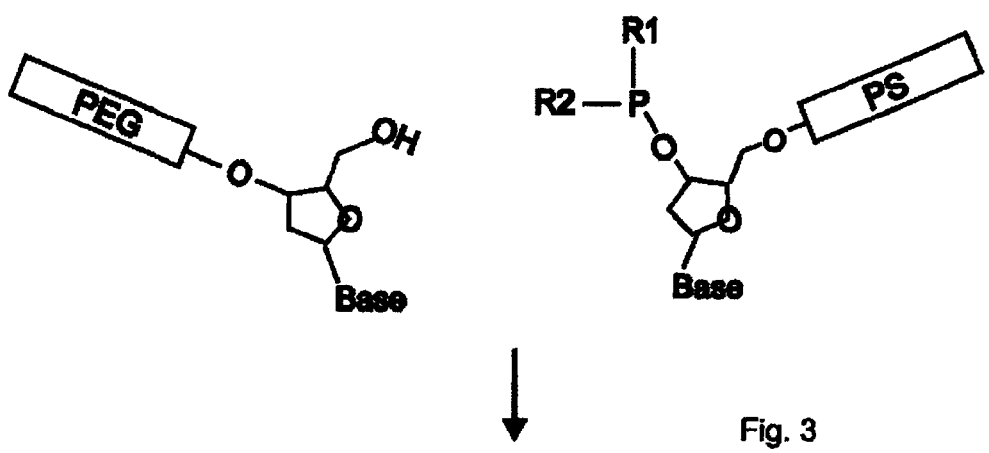
Figure 4:
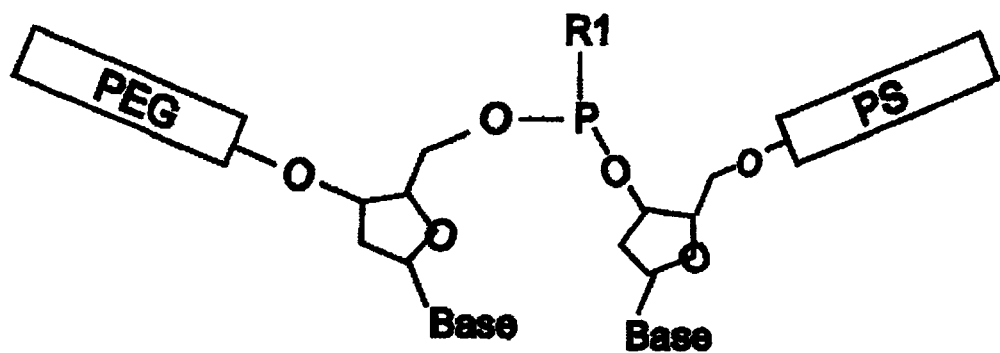
Figure 5:
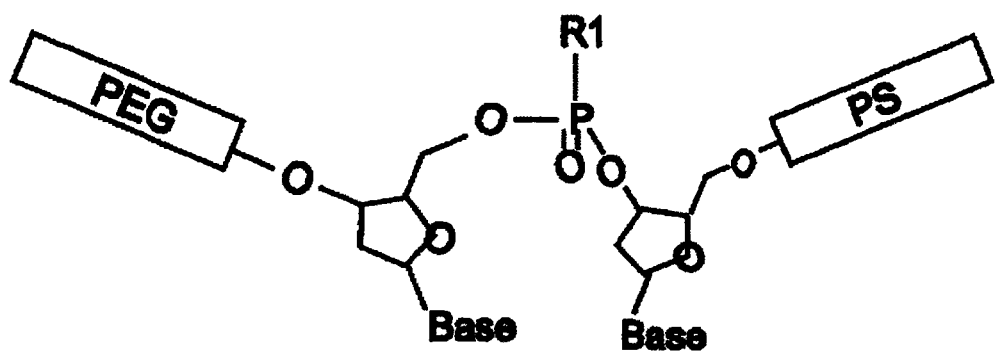
Figure 6:
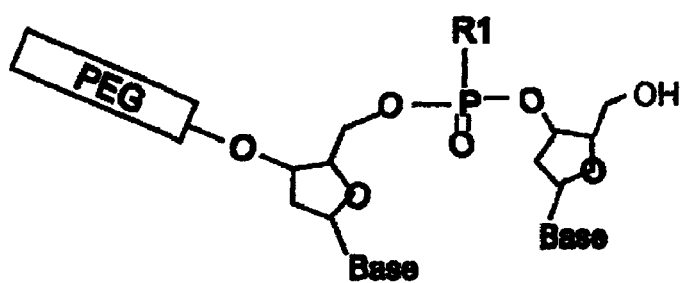
Figure 11:
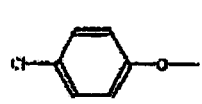
Figure 11:
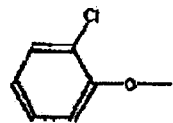
Figure 11:

After carrying out a precipitation reaction and, where appropriate, at least one washing step, the next process step, depicted in FIG. 3, comprises contacting the first compound with a nucleoside phosphoramidite as the second compound, at whose 5' oxygen atom a polystyrene (PS) group is bound. R1 is a protective group which protects the phosphate group from nucleophilic attacks during the fluid-phase synthesis. The protective group may be cleaved off after synthesis, preferably together with removal of the PEG or PS group. Examples of protective groups of this kind are depicted in FIG. 11. R2 is a diisopropylamine moiety. The phosphoramidite group is arranged on the 3' oxygen atom. The phosphoramidite group reacts with the free OH group of the first nucleotide in a condensation reaction, resulting in the formation of a dimer depicted in FIG. 4, in which the phosphorus has oxidation number +3. In order to prevent cleavage on the phosphorus during later removal of the polystyrene, the former is oxidized to oxidation number +5 by adding an aqueous iodine solution. The corresponding reaction product is depicted in FIG. 5. This reaction product may already specifically precipitate due to the addition of said aqueous iodine solution. Alternatively or additionally, non-precipitated reaction product may be precipitated together with unreacted second compound by a precipitation reaction specific for polystyrene. The reaction product is separated from any first compound which may still be present but has not reacted, for example by centrifugation, and washed, where appropriate. After dissolving the reaction product in a solvent, in which the second compound does not dissolve, a cleavage reaction is carried out in which the polystyrene is removed, producing an OH group as active group on the 5' end of the dimer. The corresponding dimer is depicted in FIG. 6.

Figure 7:
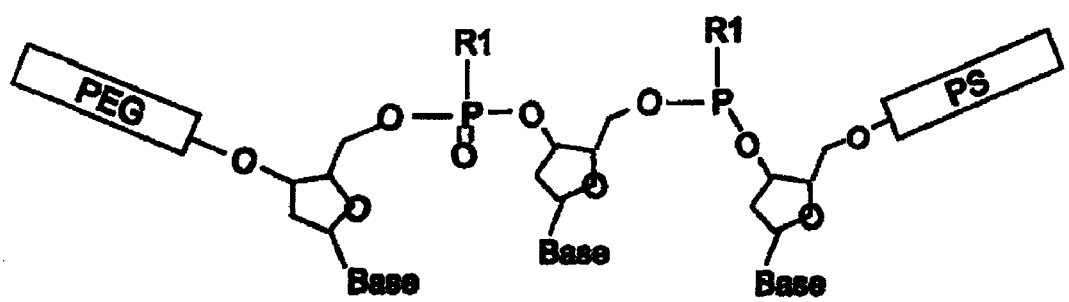
Figure 8:
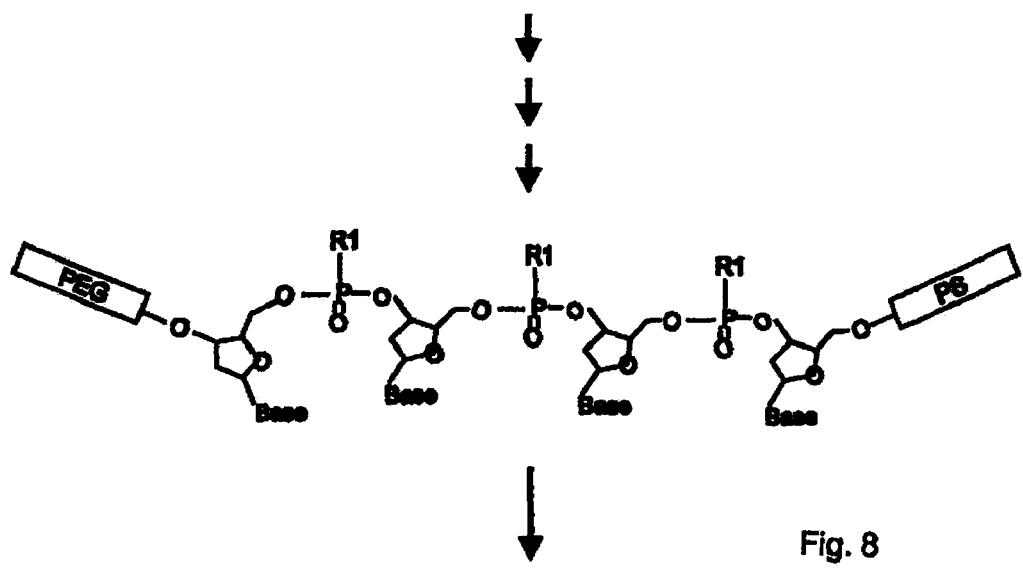
Figure 9:
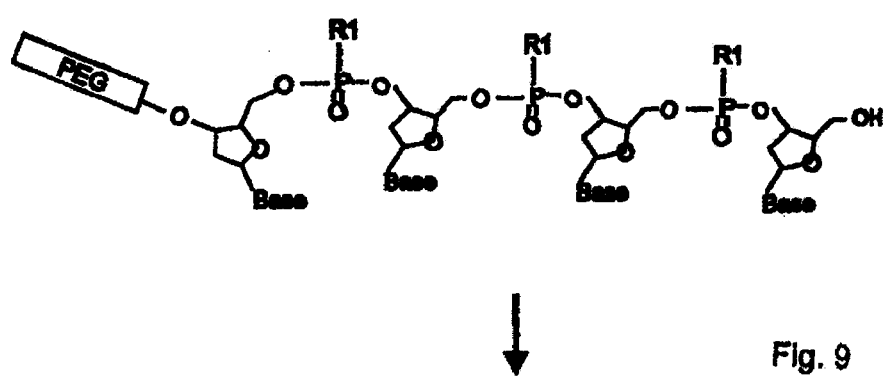
Figure 10:
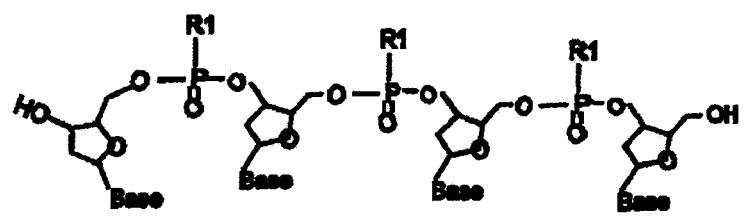

Subsequently, said dimmer, instead of the first compound, is contacted with a further nucleoside phosphoramidite with a polystyrene group bound to its 5' end as a further compound. Condensation produces the trimer depicted in FIG. 7. After oxidizing the phosphorus which has oxidation number +3 to oxidation number +5, a precipitation specific for polystyrene, again dissolving the trimer in a solvent in which the further compound does not dissolve, and cleaving off the polystyrene, the trimer is available for further condensation steps, such that a polymer of a specific length is able to be formed. An example of this is the tetramer depicted in FIG. 8. Said tetramer is precipitated in a precipitation reaction specific for polystyrene and specifically dissolved again. The reaction product remaining after cleaving off the polystyrene is depicted in FIG. 9. It is precipitated in a precipitation reaction specific for polyethylene glycol, separated and dissolved again. Subsequently, the polyethylene glycol is cleaved off in a cleavage reaction and separated in a precipitation reaction specific for polyethylene glycol from the reaction product remaining in solution and depicted in FIG. 10 (first polymer). The latter may then likewise be precipitated by a precipitation, for example by means of alcohol.

DETAILED DESCRIPTION

The essential feature of the method of the invention is that of the nascent first polymer, due to the second and third polymers which are attached thereto and can be precipitated in each case in a specific manner, being separated from unreacted monomer and from non-extended further reaction product in a simple manner after each linking reaction, thereby dispensing with a complicated purification at the end of the synthesis. Precipitates can be removed simply by centrifugation or filtration. This can be achieved in a cost-effective manner even on a large scale, in contrast to a chromatographic separation. Furthermore, the method of the invention does not cause incorrect reaction products to accumulate, thereby preventing an exponential increase in incorrect polymers as a function of increasing chain length, as is the case in conventional solid-phase synthesis. Due to dispensing with a complicated purification and preventing the production of large amounts of incorrect polymers, the costs of producing said polymer are distinctly lower than for a polymer produced using conventional methods.

The precipitation reactions may be carried out in various ways. For example, the solubility of the second or third polymer may be reduced by adding a solvent in which the respective polymer is insoluble. Polyethylene glycol (PEG), for example, may be precipitated with the aid of methyl tertiary butyl ether (MtBE). Furthermore, the "low critical solution temperature" may be utilized for precipitation. This involves an increase in temperature causing precipitation in an appropriate medium. For example, poly-(N-isopropylacrylamide) dissolved in water may be precipitated at temperatures above 30.2° C. It is also possible to utilize the "upper critical solution temperature". This involves a decrease in temperature causing precipitation in an appropriate medium. For example, PEG dissolved in acetone precipitates at temperatures below 30° C. Furthermore, polymers may be precipitated by means of a chemical precipitant, as long as precipitation is reversible, since the precipitate must be dissolved again for further coupling steps. For example, organobarium compounds may be precipitated as polymers in the form of sulfates.

In the case of oligonucleotide synthesis, another advantage of the method of the invention is that of a capping step required in conventional oligonucleotide synthesis not being necessary. Said capping step is carried out in conventional methods in order to block OH groups on the 5' carbon atom which have not reacted in the condensation, for example by acetylation by means of acetic anhydride, and thereby eliminate them from any further reaction. Since, however, the means which is used for blocking interferes with said further reaction, a further purification step is required after capping. The method of the invention also dispenses with this step. Capping is not required in the method of the invention because only the reaction product is precipitated in step e1) and only the reaction product dissolves in step e2). As a result, there are no nucleotides left in the reaction mixture which have not reacted previously and which have free OH groups.

However, if small amounts of unreacted nucleotides in the specific precipitation reaction according to step e1) or during specific dissolving according to step e2) were to be carried over, an additional capping step may be carried out in order to increase the purity of the reaction product.

In a preferred embodiment of the method, a precipitation reaction specific for the second polymer is carried out after step g) or between steps f) and g), and the further reaction product precipitated in the process and formed in step f) is separated. Alternatively, a precipitation specific for the third polymer may be carried out between steps f) and g), and the third polymer precipitated in the process and formed in step f) may be separated. Carrying out the precipitation between steps f) and g) may result in an even higher purity of the final product because the third polymer which represents a contamination after step f) has been carried out is not carried over to another reaction step.

Both the first and second monomers are preferably nucleotides. Since oligo- and polynucleotides are increasingly being used for labeling products, there is a great demand for them which can be satisfied using conventional technology only at high cost. The comparatively low amount of purification in the method of the invention is particularly noticeable in the production of oligo- and polynucleotides. 50% of the production costs of an oligo- or polynucleotide produced by conventional technology are the costs of chromatographic purification of the product.

The activatable first group may consist of an oxygen atom bound to the 5' carbon atom of the nucleotide and a protective group, in particular a dimethoxytrityl group, which is bound to said oxygen atom. The protective group may also be the third polymer, with particular preference being given to the third polymer being bound to a dimethoxytrityl group. The activatable first group may be activated by cleaving off the protective group with reduction of the oxygen atom, in particular by means of an organic acid as activator. As a result, the active group formed may be an OH group, for example. The organic acid may be a weak organic acid such as, for example, dichloroacetic acid. If the protective group is a dimethoxytrityl group, cleavage is referred to as detritylation.

The active first group may be an OH group arranged on the 5' carbon atom of the nucleotide forming the first monomer. The second monomer may be a nucleoside phosphoramidite. Preference is given to the nucleoside phosphoramidite being activated by protonation, in particular by means of H-tetrazole, ethylthiotetrazole or another tetrazole derivative or dicyanoimidazole, prior to or during contacting according to step c).

When using phosphoramidite, an oxidation step may be carried out between steps c) and g) in order to oxidize the phosphite triester formed to a phosphotriester, in particular by means of iodine as oxidant. This may prevent phosphoramidite from being cleaved off in a subsequent detritylation. The oxidant here is preferably chosen such that a bond to the dimethoxy-trityl group, which may be present, is also cleaved by an oxidation reaction.

Preference is given to the first monomer being bound via an oxygen atom, in particular within an ether bond or an ester bond, to the second polymer. In the linking reaction, the first compound may be linked via a further oxygen atom, in particular within an ether bond or an ester bond, to the second compound. After repeating steps b) to f) (n−2) times, the first cleavage reaction may be carried out in order to separate the first polymer formed from the second polymer. This is not necessary, if the fact that the second polymer is connected to the first polymer does not interfere with the further use of said first polymer or is even useful therefor. This may be the case, in particular, if the polymer formed is a polynucleotide used as capture molecule and the target polynucleotides hybridizing therewith are to be precipitated by a specific reaction.

In the course of the first cleavage reaction, the phosphotriester formed may be reduced. The first cleavage reaction may be carried out, for example, by means of an ammonium hydroxide solution.

In a preferred embodiment of the method of the invention, the second or the third polymer is polyethylene glycol. The third or second polymer may also be polystyrene. In any case, however, the second and third polymers are different.

The invention is illustrated in more detail below on the basis of the diagrammatic representation in FIGS. 1 to 11 and an exemplary embodiment.

The invention claimed is:

1. A method for fluid-phase synthesis of a first polymer formed from n monomers, comprising the following steps:
   a) providing a dissolved first compound, wherein said first compound is formed from a first monomer and a second polymer having a first specific solubility, wherein said first monomer and said second polymer are linked to one another by a first bond, wherein said first bond can be cleaved by a first cleavage reaction, wherein said first monomer has an active or an activatable first group,
   b) providing a dissolved second compound, wherein said second compound is formed from a second monomer and a third polymer having a second specific solubility, wherein said second monomer and said third polymer are linked to one another by a second bond, wherein said second bond can be cleaved by a second cleavage reaction, wherein said second monomer has an active or an activatable second group which, by way of a linking reaction, can react with the first group with formation of a third bond between the first and second monomers, wherein said first and second specific solubilities are different,
   c) contacting the first and second compounds in order for the linking reaction to occur, wherein, if the activatable first and/or the activatable second group are/is present, said first and/or said second group are/is activated by adding an activator,
   d) carrying out a precipitation reaction specific for the second or third polymer, and separating any first or second compound precipitated in the process and the reaction product formed in step c),
   e1) dissolving the separated first or second compound and the reaction product in a solvent, carrying out a precipitation reaction specific for the second or third polymer for which the precipitation reaction carried out in step d) was not specific, separating reaction products precipitated in the process, and dissolving the reaction product in said solvent or another solvent,
   or e2) contacting the separated first or second compound and the reaction product with a solvent in which essentially only the reaction product dissolves but in which the first or second compound precipitated in step d) essentially does not dissolve,
   f) carrying out the second cleavage reaction with the reaction product, wherein a further reaction product and the third polymer are formed, wherein the first active group is formed on said further reaction product, and
   g) (n−2)-fold repetition of steps b) to f), wherein the first compound is replaced by the further reaction product formed in step f), and the second compound is replaced in each case with a further compound, wherein said further compound is formed from a further monomer and the third polymer, wherein both the first and second monomers are nucleotides and wherein the precipitation reaction specific for the second polymer is a precipitation reaction in which the third polymer essentially remains in solution and the precipitation reaction specific for the third polymer is a precipitation reaction in which the second polymer essentially remains in solution, and wherein the second polymer is polyethylene glycol and the third polymer is polystyrene or wherein the second polymer is polystyrene and the third polymer is polyethylene glycol.

2. The method as claimed in claim 1, wherein, after step g) or between steps f) and g), a precipitation specific for the second polymer is carried out, and the further reaction product precipitated in the process and formed in step f) is separated, or a precipitation specific for the third polymer is carried out, and the third polymer precipitated in the process and formed in step f) is separated.

3. The method as claimed in claim 1, wherein the activatable first group consists of an oxygen atom bound to the 5' carbon atom of the nucleotide and a protective group, the third polymer, or the third polymer bound to a dimethoxytrityl group, which protective group is bound to said oxygen atom.

4. The method as claimed in claim 3, wherein the activatable first group is activated by cleaving off the protective group with reduction of the oxygen atom.

5. The method as claimed in claim 1, wherein the active first group is an OH group arranged on the 5' carbon atom of the nucleotide forming the first monomer.

6. The method as claimed in claim 1, wherein the second monomer is a nucleoside phosphoramidite.

7. The method as claimed in claim 6, wherein the nucleoside phosphoramidite is activated by protonation prior to or during contacting according to step c).

8. The method as claimed in claim 6, wherein an oxidation step is carried out between steps c) and g) in order to oxidize the phosphite triester formed to a phosphotriester.

9. The method as claimed in claim 1, wherein the first monomer is bound via an oxygen atom.

10. The method as claimed in claim 1, wherein the first cleavage reaction is carried out after repeating steps b) to f) (n−2) times, according to step g).

11. The method as claimed in claim 10, wherein the second monomer is a nucleoside phosphoramidite, wherein an oxidation step is carried out between steps c) and g) in order to oxidize the phosphite triester formed to a phosphotriester, wherein the phosphotriester is reduced in the course of the first cleavage reaction.

12. The method as claimed in claim 10, wherein the first cleavage reaction is carried out by means of an ammonium hydroxide solution.

13. The method of claim 3, wherein the protective group is a dimethoxytrityl group.

14. The method of claim 4, wherein the activatable first group is activated by means of an organic acid as activator.

15. The method of claim 7, wherein the nucleoside phosphoramidite is activated by protonation by means of H tetrazole, ethylthiotetrazole or another tetrazole derivative or dicyanoimidazole.

16. The method of claim 8, wherein the oxidation step is carried out by means of iodine as oxidant.

17. The method of claim 9, wherein the first monomer is bound via an oxygen atom within an ether bond or an ester bond.

18. The method of claim 11, wherein the oxidation step is carried out by means of iodine as oxidant.

* * * * *